United States Patent
Sasai (10) Patent No.: US 8,779,393 B2
(45) Date of Patent: Jul. 15, 2014

(54) CHARGED PARTICLE BEAM IRRADIATION SYSTEM AND NEUTRON BEAM IRRADIATION SYSTEM

(75) Inventor: Kenzo Sasai, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 118 days.

(21) Appl. No.: 13/415,459

(22) Filed: Mar. 8, 2012

(65) Prior Publication Data

US 2012/0228522 A1 Sep. 13, 2012

(30) Foreign Application Priority Data

Mar. 10, 2011 (JP) ................ P2011-053248

(51) Int. Cl.
*A61N 5/10* (2006.01)
(52) U.S. Cl.
USPC ................. 250/492.1; 250/492.3; 250/396 R
(58) Field of Classification Search
CPC ....................................................... G21K 5/02
USPC ..................................................... 250/492.1
See application file for complete search history.

(56) References Cited

U.S. PATENT DOCUMENTS

| | | | | |
|---|---|---|---|---|
| 4,112,306 | A | * | 9/1978 | Nunan .......................... 376/112 |
| 4,139,777 | A | * | 2/1979 | Rautenbach .................. 376/112 |
| 5,818,058 | A | | 10/1998 | Nakanishi et al. |
| 7,030,399 | B2 | * | 4/2006 | Williamson et al. ....... 250/515.1 |
| 2009/0200483 | A1 | * | 8/2009 | Gall et al. ................. 250/396 R |

FOREIGN PATENT DOCUMENTS

| | | |
|---|---|---|
| JP | S53-14297 | 2/1978 |
| JP | H7-255867 A | 10/1995 |
| JP | H9-192244 A | 7/1997 |
| JP | H10-326699 A | 12/1998 |
| JP | 2003-024459 A2 | 1/2003 |
| JP | 2009-515671 A | 4/2009 |
| JP | 2010-151617 A2 | 7/2010 |
| WO | 03/018132 A1 | 3/2003 |

OTHER PUBLICATIONS

Japanese Office Action dated May 20, 2014 for corresponding Japanese Application No. 2011-053248.

* cited by examiner

*Primary Examiner* — Phillip A Johnston
(74) *Attorney, Agent, or Firm* — Squire Patton Boggs (US) LLP (57) ABSTRACT

A charged particle beam irradiation system includes: an accelerator which accelerates charged particles along an orbit, thereby emitting a charged particle beam; a gantry on which the accelerator is mounted and which can rotate or oscillate around a given axis; and an irradiation section which is mounted on the gantry and can irradiate the charged particle beam emitted from the accelerator, toward an irradiated body, wherein a shielding body which is provided in the gantry and shields radiation that is radiated from a side of the accelerator, which may be a face intersecting the radial direction of the orbit, is disposed.

7 Claims, 11 Drawing Sheets

CHARGED PARTICLE BEAM IRRADIATION SYSTEM AND NEUTRON BEAM IRRADIATION SYSTEM

CROSS-REFERENCE TO RELATED APPLICATION

Priority is claimed to Japanese Patent Application No. 2011-053248, filed Mar. 10, 2011, the entire content of which is incorporated herein by reference.

BACKGROUND OF THE INVENTION

1. Field of the Invention

The present invention relates to a charged particle beam irradiation system and a neutron beam irradiation system.

2. Description of the Related Art

Equipment which irradiates a patient with charged particles such as a proton beam so as to perform cancer treatment has been known. This type of equipment is provided with a particle accelerator which accelerates ions (charged particles) produced by an ion source, a transport line which transports the charged particles accelerated by the accelerator, and a rotatable irradiation device (a rotating gantry) which irradiates a patient with the charged particles from any direction.

In a charged particle beam therapy system described in the related art, a beam generation particle accelerator is mounted on a rotating gantry. The accelerator is supported on the rotating gantry in such a manner that a beam emitted from the accelerator is directly irradiated to a patient.

SUMMARY OF THE INVENTION

According to an exemplary embodiment, there is provided a charged particle beam irradiation system including: an accelerator which accelerates charged particles along an orbit, thereby emitting a charged particle beam; a gantry on which the accelerator is mounted and which can rotate or oscillate around a given axis; and an irradiation section which is mounted on the gantry and can irradiate the charged particle beam emitted from the accelerator, toward an irradiated body, wherein a shielding body which is provided in the gantry and shields radiation that is radiated from a side of the accelerator, which is a face intersecting the radial direction of the orbit, is disposed.

Further, according to another embodiment, there is provided a neutron beam irradiation system including: an accelerator which accelerates charged particles along an orbit, thereby emitting a charged particle beam; a gantry on which the accelerator is mounted and which can rotate or oscillate around a given axis; a neutron beam generation section which is irradiated with the charged particle beam emitted from the accelerator, thereby generating a neutron beam; and an irradiation section which is mounted on the gantry and can irradiate the neutron beam generated in the neutron beam generation section, toward an irradiated body, wherein a shielding body which is provided in the gantry and shields radiation that is radiated from a side of the accelerator, which is a face intersecting the radial direction of the orbit, is disposed.

DESCRIPTION OF THE PREFERRED EMBODIMENTS

In the related art, there is a concern that some of the accelerated charged particles may collide with components such as an electrode or a magnetic pole for generating a magnetic field in the accelerator and secondary radiation (neutron beam, gamma rays, or the like) which are generated at the time of the collision may advance in a direction in which a patient is present. Therefore, it is required to reduce or prevent exposure of the patient by the secondary radiation which is generated by such a collision of the charged particles with the components in the accelerator and radiated from a side of the accelerator.

It is desirable to provide a charged particle beam irradiation system and a neutron beam irradiation system in which by mounting an accelerator which accelerates charged particles on a rotating gantry, it is possible to reduce the fear of exposure by secondary radiation which is generated from the accelerator, while attaining space-saving.

According to the charged particle beam irradiation system and the neutron beam irradiation system related to the invention, since the accelerator which accelerates the charged particles and the irradiation section which performs irradiation of the charged particle beam emitted from the accelerator (or the neutron beam generated by irradiation of the charged particle beam) are mounted on the gantry, it is possible to reduce the overall size of the apparatus for irradiating the charged particle beam or the neutron beam. Further, since the entire apparatus is united and configured in an integrated fashion, assembly in advance at a factory or the like becomes possible, and it is also possible to transport an apparatus assembled at a factory to an installation site and install it as is.

Further, in the charged particle beam irradiation system and the neutron beam irradiation system, since the shielding body which shields the radiation is disposed between the side of the accelerator and the irradiated body, secondary radiation which is radiated from the side of the accelerator is shielded by the shielding body. In this way, since the secondary radiation which is generated due to collision of the charged particles with components such as a magnetic pole or an electrode in the accelerator is shielded by the shielding body, it is possible to suppress exposure of a patient to the secondary radiation which is generated from the accelerator and radiated from the side thereof.

Here, the shielding body may be disposed only at a position where the radiation which is radiated from the portion of the side that faces the irradiated body is shielded, in a circumferential direction of the orbit. In this way, it is possible to make a configuration in which the shielding body is disposed only at a portion in a direction in which the irradiated body is present, for example, in the side of the accelerator and the shielding body is not disposed at a side portion in a direction in which the irradiated body is not present. For this reason, it is possible to effectively dispose the shielding body and it is possible to omit the installation space of the shielding body. As a result, it is possible to suppress an increase in the size of the accelerator having the shielding body at the side thereof. Further, it is possible to suppress an increase in the weight of the gantry.

Further, the charged particle beam irradiation system may include an irradiation chamber which is provided in the gantry and in which the irradiated body is irradiated with the charged particle beam, and the shielding body may be supported on a wall section constituting the irradiation chamber. In this way, by mounting the shielding body on the wall section constituting the irradiation chamber, it is possible to make the shielding body not be mounted on the accelerator. For this reason, for example, when performing maintenance (checking, repair, or the like) of the accelerator, it is not necessary to remove the shielding body, so that it is possible to easily perform the maintenance.

Further, the shielding body may be disposed so as to cover the entire circumference of the side of the accelerator, and a cutout portion may be formed on a charged particle beam emitting opening side of the shielding body. In this way, the radiation which is radiated from the side of the accelerator can be shielded over the entire circumference.

Further, the charged particle beam irradiation system may include an energy selection section which is provided on a transport line transporting the charged particles emitted from the accelerator and makes charged particles having a desired energy width among the charged particles selectively pass therethrough, and another shielding body which shields the radiation may be disposed between the energy selection section and the irradiated body. In the energy selection section which makes charged particles having a desired energy width selectively pass therethrough, charged particles having an energy width which is not selected collide with components in the energy selection section without passing through the energy selection section. At this time, since the secondary radiation is generated due to the collision of the charged particles, by disposing the shielding body between the energy selection section and the irradiated body, the secondary radiation is shielded. In this way, it is possible to reduce the fear of exposure due to the secondary radiation which is generated in the energy selection section.

Further, the shielding body may be configured by laminating a plurality of different materials in a thickness direction of the shielding body. In this way, by disposing a material in which ability to shield the secondary radiation having high energy is high on the side surface side of the accelerator and disposing a material in which ability to shield the secondary radiation having low energy is high on the outer side, for example, in the thickness direction of the shielding body, it is possible to reduce the size of the shielding body.

Hereinafter, exemplary embodiments of a charged particle beam irradiation system will be described referring to the drawings. In these exemplary embodiments, a description will be performed with respect to a case where the charged particle beam irradiation system is set to be a proton therapy system. The proton therapy system is applied to cancer treatment, for example, and is an apparatus which irradiates a tumor (an irradiation target) in a patient's body with a proton beam (a charged particle beam).

First Embodiment

Figure 1:
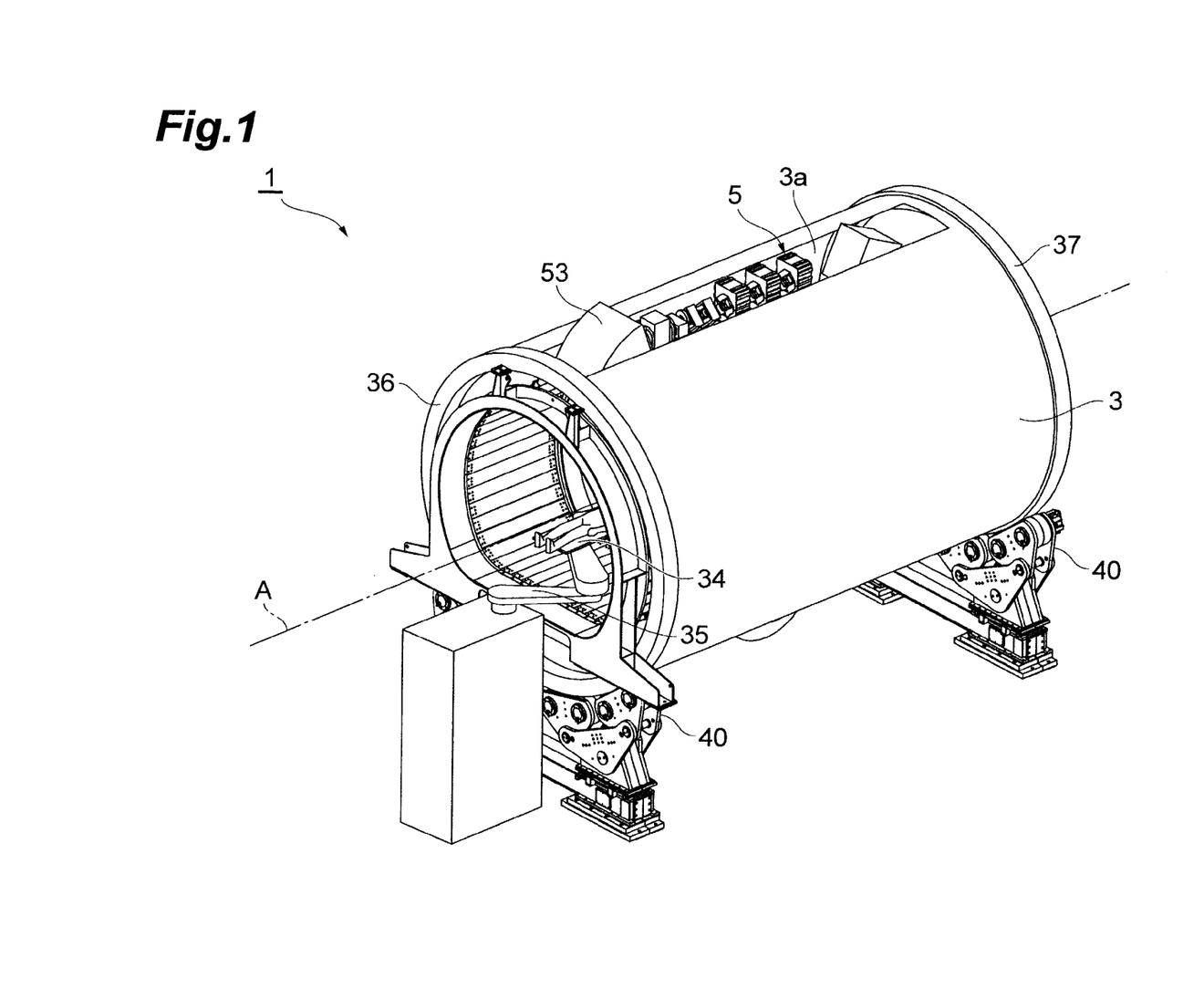
FIG. 1 is a perspective view showing an overview of a proton therapy system (a charged particle beam irradiation system) according to an exemplary embodiment.

First, a proton therapy system 1 according to a first embodiment will be described with reference to FIGS. 1 to 3. FIG. 1 is a perspective view showing an overview of the proton therapy system 1 according to this embodiment, FIG. 2 is a perspective cross-sectional view in partially cut away in which half of a rotating section is removed along the axis of rotation of the rotating section from FIG. 1, and FIG. 3 is a vertical cross-sectional view along the axis of rotation of the proton therapy system in FIG. 1.

Figure 2:
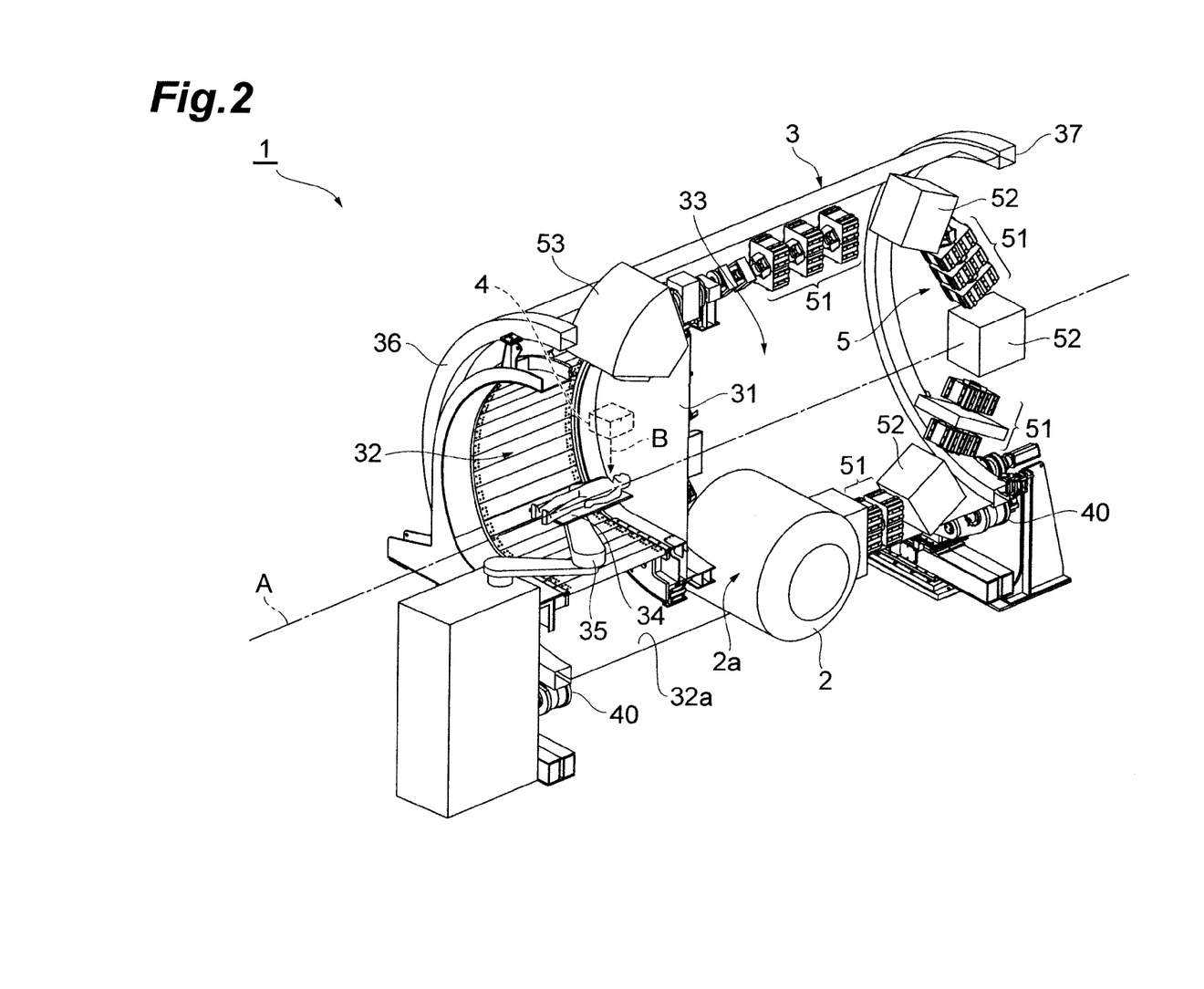
FIG. 2 is a perspective cross-sectional view in partially cut away in which half of a rotating section is removed along the axis of rotation of the rotating section from FIG. 1.
Figure 3:
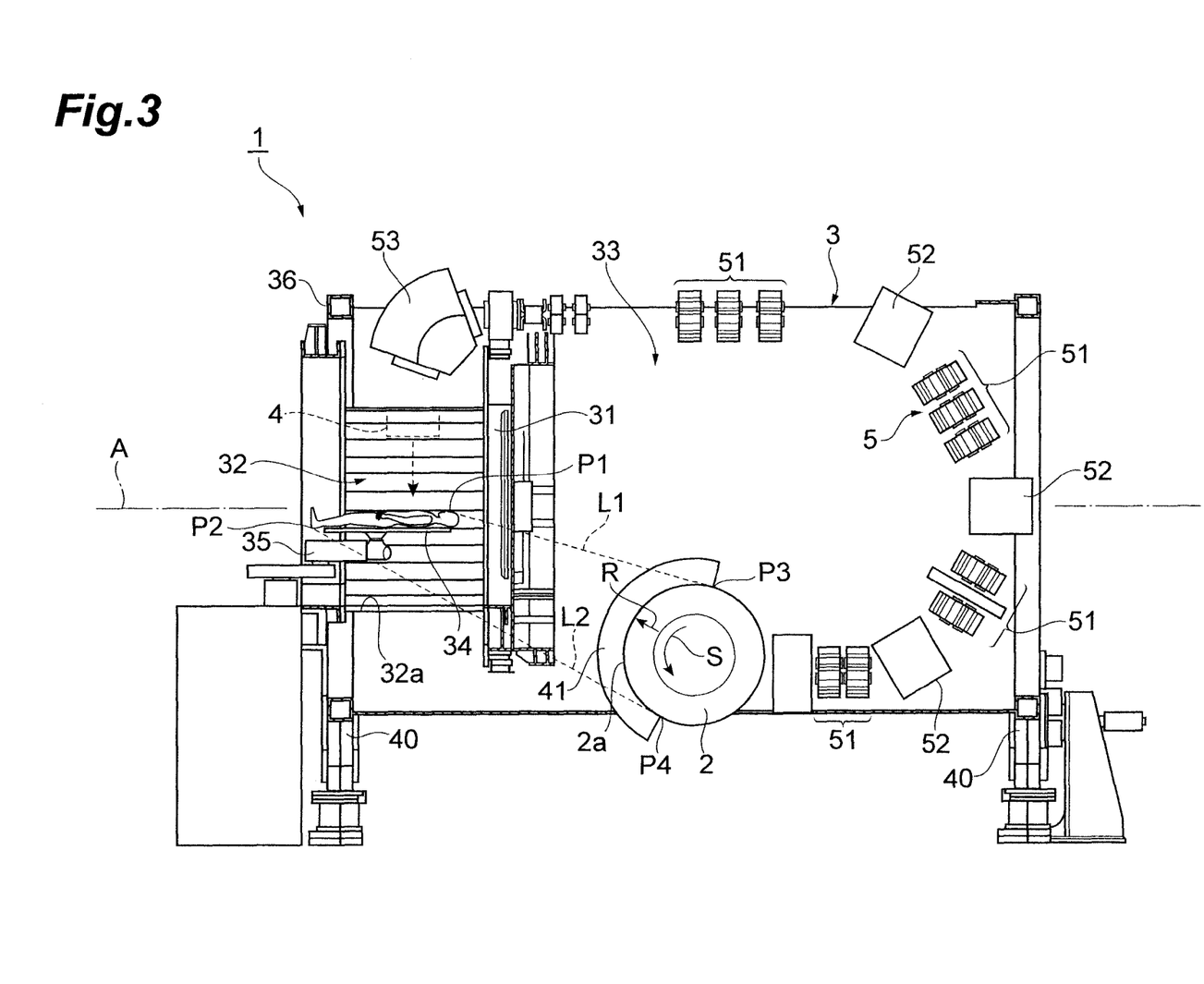
FIG. 3 is a vertical cross-sectional view of the proton therapy system in FIG. 1.

As shown in FIGS. 1 to 3, the proton therapy system 1 is configured to include a cyclotron (a particle accelerator) 2 which produces a proton beam, an outer shell section (a gantry) 3 having a cylindrical shape and capable of rotating 360° around the axis of rotation, an irradiation section 4 capable of irradiating the irradiation target with the proton beam, and a transport line 5 which transports the proton beam produced by the cyclotron 2 to the irradiation section 4.

The cyclotron 2 accelerates ions (a cation of hydrogen) which are supplied from an ion source (not shown), in the inside of a vacuum box (not shown), thereby producing the proton beam. In the inside of the cyclotron 2, in order to form a magnetic field for accelerating the ions, components (not shown) such as an electromagnet (an iron yoke) and an electrode are disposed. The ions are accelerated along a spiral trajectory (an orbit) by the formed magnetic field. In the cyclotron 2, after the ions are accelerated, the proton beam is emitted. The cyclotron 2 communicates with the transport line 5 and the produced proton beam is introduced into the transport line 5.

The outer shell section (the gantry) 3 is a cylindrical body having a thin-walled structure, as shown in FIGS. 1 and 2, and is configured so as to be able to have a lighter weight while maintaining rigidity. The outer shell section 3 is supported by roller devices 40 disposed below the outer shell section 3, so as to be able to rotate around a cylindrical axis A. The outer shell section 3 comes into contact with the roller devices 40 at the outer circumferential surfaces in the vicinity of both end portions of the cylindrical shape, and if the roller devices 40 are driven by motors (not shown), rotary power is imparted to the outer shell section 3. Further, rotation of the outer shell section 3 is stopped by a braking device (not shown). In addition, the entire length in the axial direction of the outer shell section 3 is 8 m, for example, and the diameter is 6 m, for example. In addition, the gantry may also have a configuration having no cylindrical body and may also have a configuration having a frame body capable of oscillating by 180° around the axis A (refer to FIG. 8, for example).

The outer shell section 3 has, in the inside thereof, a partition plate 31 approximately perpendicular to the axis A (a given axis), as shown in FIG. 2. The inside of the outer shell section 3 is partitioned into two areas, an area for treatment (an irradiation chamber) 32 and an area for proton beam production (a beam production chamber) 33, in the axial direction by the partition plate 31. Further, in the proton therapy system 1 according to this embodiment, as shown in FIG. 3, a shielding shield 41 is provided between a side 2a of the cyclotron 2 and a treatment table 34 (the details will be described later). In addition, in FIG. 2, for clarification of the drawing, illustration of the shielding shield 41 provided at a side portion of the cyclotron 2 is omitted.

In the area for treatment 32, the treatment table 34 on which a patient for proton therapy lies down is disposed. At the time of proton beam irradiation, the treatment table 34 is disposed in the vicinity of the axis of rotation A of the outer shell section 3 by a movement section 35. Further, the treatment table 34 can be moved between the outside and the inside (the area for treatment 32) of the proton therapy system 1 through an opening of an end portion 36 on the area for treatment 32 side of the outer shell section 3 by the movement section 35.

Further, in the area for treatment 32 of the outer shell section 3, the irradiation section 4 is fixedly installed in such a manner that irradiation of a beam is performed in a direction B which is directed to the axis of rotation A of the outer shell section 3. The irradiation section 4 freely rotates around the treatment table 34 with the rotation of the outer shell section 3, so that a patient on the treatment table 34 can be irradiated with the proton beam from any direction around the axis of rotation of the outer shell section 3. In addition, provided that the irradiation section 4 can rotate with the rotation of the gantry, the irradiation section 4 may also be mounted at another position and may also be mounted, for example, on the inner circumferential surface of the outer shell section 3, an end portion of a bending magnet 53, or the like.

The transport line 5 is connected at a starting end thereof to the cyclotron 2 and at a terminus thereof to the irradiation section 4 and transports the proton beam accelerated in the cyclotron 2 to the irradiation section 4. The transport line 5 includes a plurality of quadrupole electromagnets 51 which converges the proton beam, a plurality of (in FIG. 2, three) ESSs (energy selection systems or energy selection sections) 52 which adjusts the irradiation energy of the proton beam, and the like, and the transport line 5 has the bending magnet (a deflection magnet) 53 which causes curvature the proton beam (in this embodiment, by about 90 degrees), thereby determining an incident direction of the proton beam on the irradiation section 4, at a position just before the transport line 5 is connected to the irradiation section 4 at the terminus thereof. The bending magnet 53 is installed in a centrifugal direction of the outer shell section 3 from the irradiation section 4 in the area for treatment 32, as shown in FIG. 2. In addition, in the transport line 5, a beam transport tube (not shown) is provided over the entirety thereof along the trajectory of the proton beam.

The ESS 52 is for selectively extracting a proton beam having a desired energy width from the proton beams having a given energy distribution, which have been transported. In the ESS 52, a plurality of slits is provided, and by setting the slit through which the proton beam can pass, the ESS 52 makes only charged particles having a desired energy width selectively pass therethrough. In other words, by closing the other slits, the ESS 52 makes a proton beam not having the desired energy width not pass therethrough.

In particular, in this embodiment, the outer shell section 3 having a cylindrical shape is configured so as to function as an outer shell of the whole of the proton therapy system 1 and be able to attain a reduction in weight while maintaining the rigidity of the entire apparatus. Further, at least some of the respective elements of the cyclotron 2 and the transport line 5 are accommodated inside the outer shell section 3 and held by the outer shell section 3. Here, the express "being held by the outer shell section 3" specifically means the state of being directly mounted on the inner surface of the outer shell section 3 or the state of being connected to the inner surface of the outer shell section 3 through members such as brackets. Then, due to such a configuration, the proton therapy system 1 according to this embodiment has a compact configuration in which all constituent elements related to proton therapy are united in an integrated fashion.

The cyclotron 2 is held by the outer shell section 3 at a position opposed to the position of the terminus (at least the bending magnet 53) of the transport line 5 around the axis of rotation A of the outer shell section 3, as shown in FIG. 2. In other words, the cyclotron 2 and the bending magnet 53 are respectively held by the outer shell section 3 at positions opposed to each other at an angle of 180° centered on the axis of rotation A when viewed at the line of sight parallel to the axis of rotation A of the outer shell section 3, more specifically, positions symmetrical to each other with the axis of rotation A interposed therebetween when viewed at the line of sight parallel to the axis of rotation A. By disposing the cyclotron 2 and the bending magnet 53 in this manner, the cyclotron can be used as a counter weight of the bending magnet, so that a separate counter weight can be omitted.

The transport line 5 first extends parallel to a direction of the axis A of the outer shell section 3 along the inner circumferential surface of the outer shell section 3 from the starting end which is connected to the cyclotron 2 toward an end portion 37 (the opposite side to the end portion 36 on the area for treatment 32 side) on the area for proton beam production 33 side, as shown in FIG. 2. Next, the transport line 5 is curved by 180° by using the three ESSs 52 in the vicinity of the end portion 37 of the inside of the outer shell section 3 while passing through the axis A of the outer shell section 3, to extend to the inner circumferential surface of the outer shell section 3, which is opposed to the position of the starting position. Then, the transport line 5 extends parallel to the direction of the axis A to the bending magnet 53 in the area for treatment 32 along the inner circumferential surface of the outer shell section 3.

That is, the respective elements of the cyclotron 2 and the transport line 5 are disposed into an approximate U-shape on an imaginary plane (equivalent to a cross-section of the outer shell section 3 in FIG. 2) extending in the diametrical direction of the cylindrical body along the axis of rotation A of the outer shell section 3. In addition, disposition of the respective elements of the cyclotron 2 and the transport line 5 is not limited to the disposition in an approximate U-shape and may also be another disposition and, for example, the respective elements of the cyclotron 2 and the transport line 5 may also be disposed into an approximate L-shape. Disposition is also acceptable in which the cyclotron 2 is disposed on the lower side and the transport line 5 extends upward from the cyclotron 2, is bent at the upper side, and then extends in the horizontal direction to be connected to the irradiation section 4.

In addition, the respective elements of the cyclotron 2 and the transport line 5 are preferably held on the inner surface of the outer shell section 3. However, a configuration is also acceptable in which some of the elements may protrude to the outer circumferential surface side of the outer shell section 3, thereby being exposed, and at least some of them are on the inner surface side of the outer shell section 3. For example, in the example shown in FIGS. 1 and 2, the outer shell section 3 has a rectangular cutout portion 3a which is opened to the upper side and extends along the transport line 5. Then, the quadrupole electromagnet 51 and the bending magnet 53 are exposed through the cutout portion 3a when viewed from the outside of the outer shell section 3. As in this example, by adopting a configuration in which some of the cyclotron 2 and the transport line 5 are exposed to the outside of the outer shell section 3, since it is possible to access the cyclotron 2 or the transport line 5 through the cutout portion 3a from the outside of the outer shell section 3, as necessary, and it is possible to perform maintenance from the outside of the outer shell section 3, maintenance ability is improved.

Further, the cyclotron 2 is generally formed into a columnar form having a central axis in order to revolve and accelerate protons in the inside of a vacuum box. As shown in FIG. 2, the cyclotron 2 may also be disposed such that the central axis thereof is perpendicular to the axis A of the outer shell section 3 and may also be disposed parallel to the axis of the outer shell section 3.

Here, in the proton therapy system 1 according to this embodiment, as shown in FIG. 3, a shielding shield 41 is installed on the surface of the side 2a of the cyclotron 2. The side 2a of the cyclotron 2 forms a face intersecting the radial direction R of the orbit S of a cation. A configuration is made in which the shielding shield 41 is disposed to be limited only to a portion in a direction in which the treatment table 34 (a patient or the irradiated body) is present, in the side 2a of the cyclotron 2 and the shielding shield 41 is not disposed on the side surface of a portion in a direction in which the treatment table 34 is not present. The side surface in a direction in which the treatment table 34 is not present is not covered by the shielding shield 41 and is exposed.

The cyclotron 2 is disposed below the treatment table 34 and on the backside of the partition plate 31 in a state shown in FIG. 3. The shielding shield 41 is disposed only on the side 2a of the cyclotron 2 between a tangent line L1 which passes through an end portion (a parietal) P1 on one side of a patient lying on the treatment table 34 and a tangent line L2 which passes through an end portion (feet) P2 on the other side of the patient. Specifically, the shielding shield 41 is disposed between a contact point P3 of the tangent line L1 with the side 2a and a contact point P4 of the tangent line L2 with the side 2a in the circumferential direction S, and in the side where the shielding shield 41 is not disposed, the cyclotron 2 is exposed. The shielding shield 41 is disposed only at the portion in a direction in which the treatment table 34 (a patient or the irradiated body) is present, in the side 2a of the cyclotron 2 such that the treatment table 34 and the patient are not directly irradiated with radiation which is radiated from the side 2a of the cyclotron 2. By disposing the shielding shield 41 in this manner, a shielding body is disposed at a position where only the radiation which is radiated from the portion of the side 2a which faces the irradiated body (34) is shielded, in the circumferential direction S of the orbit.

In addition, since the height of the patient varies by individual, when setting the size of the shielding shield 41, the size of the shielding shield 41 is set to have some room for a patient's height (taking into account a greater height) so as to be able to cope with even very tall patients.

The shielding shield 41 is formed of a material which shields the radiation (gamma rays and neutron beamradiation). As a material applicable to the shielding shield 41, for example, iron, polyethylene, or the like can be given. Further, a material in which boron or the like is added to polyethylene may also be applied to the shielding shield 41.

Further, the shielding shield 41 is fixed, for example, to a support section (not shown) provided on the side of the cyclotron 2 by using bolts.

According to the proton therapy system 1, since the cyclotron 2 and the transport line 5 are at least partially accommodated in the outer shell section 3 having a cylindrical shape, constituent elements (the cyclotron 2, the transport line 5, and the irradiation section 4) required for irradiation of a proton beam are united as an integrated apparatus, so that it is possible to reduce the overall size of the apparatus. Further, since the whole of the proton therapy system 1 is united and configured in an integrated fashion, assembly at a factory or the like in advance also becomes possible, and it is also possible to transport an apparatus assembled at a factory to an installation site and install it as is. The need to assemble the apparatus at an installation site thereof is eliminated. For this reason, if an apparatus is assembled at a factory or the like in advance, the process up to a performance test at an installation site can be shortened and it also becomes possible to carry out a performance test at a factory in advance. As a result, since a reduction in size and shortening of the installation process becomes possible, the option of an installation location of the proton therapy system 1 is expanded, so that it is possible to attain improvement in versatility. Further, since a structure is taken in which the whole of the proton therapy system 1 is covered by the outer shell section 3 having a tubular shape, it is possible to reduce weight while maintaining rigidity. Then, since it is possible to maintain rigidity, it is possible to suppress flexure of the apparatus due to, for example, the weight or the like of the cyclotron 2, thereby preventing occurrence of shift of an isocenter (an intersection point of the axis of rotation A with the center line of a proton beam) of the irradiation section 4, so that it is possible to improve an irradiation system of the proton beam.

Further, according to the proton therapy system 1, since the shielding shield 41 is disposed between the side of the cyclotron 2 and the treatment table 34, secondary radiation which is radiated from the cyclotron 2 is shielded. In this way, the secondary radiation which is generated due to collision of cations with components such as a magnetic pole or an electrode in the cyclotron 2 is shielded by the shielding shield 41 provided on the side. As a result, it is possible to suppress exposure of a patient to the secondary radiation which is generated in the cyclotron 2 and radiated from the side. In addition, since the secondary radiation from the portion which is not shielded collides with the inner circumferential surface or the like of the outer shell section 3, thereby being attenuated, the influence by the secondary radiation which is reflected in the outer shell section 3 becomes small.

Further, since the shielding shield 41 is disposed only on the side in a direction in which the treatment table 34 is present, in the circumferential direction S of the orbit of the cation, it is possible to effectively dispose the shielding shield 41 and it is possible to omit an installation space of the shielding shield 41. As a result, it is possible to suppress an increase in the size and an increase in the weight of the apparatus.

Second Embodiment

Figure 4:
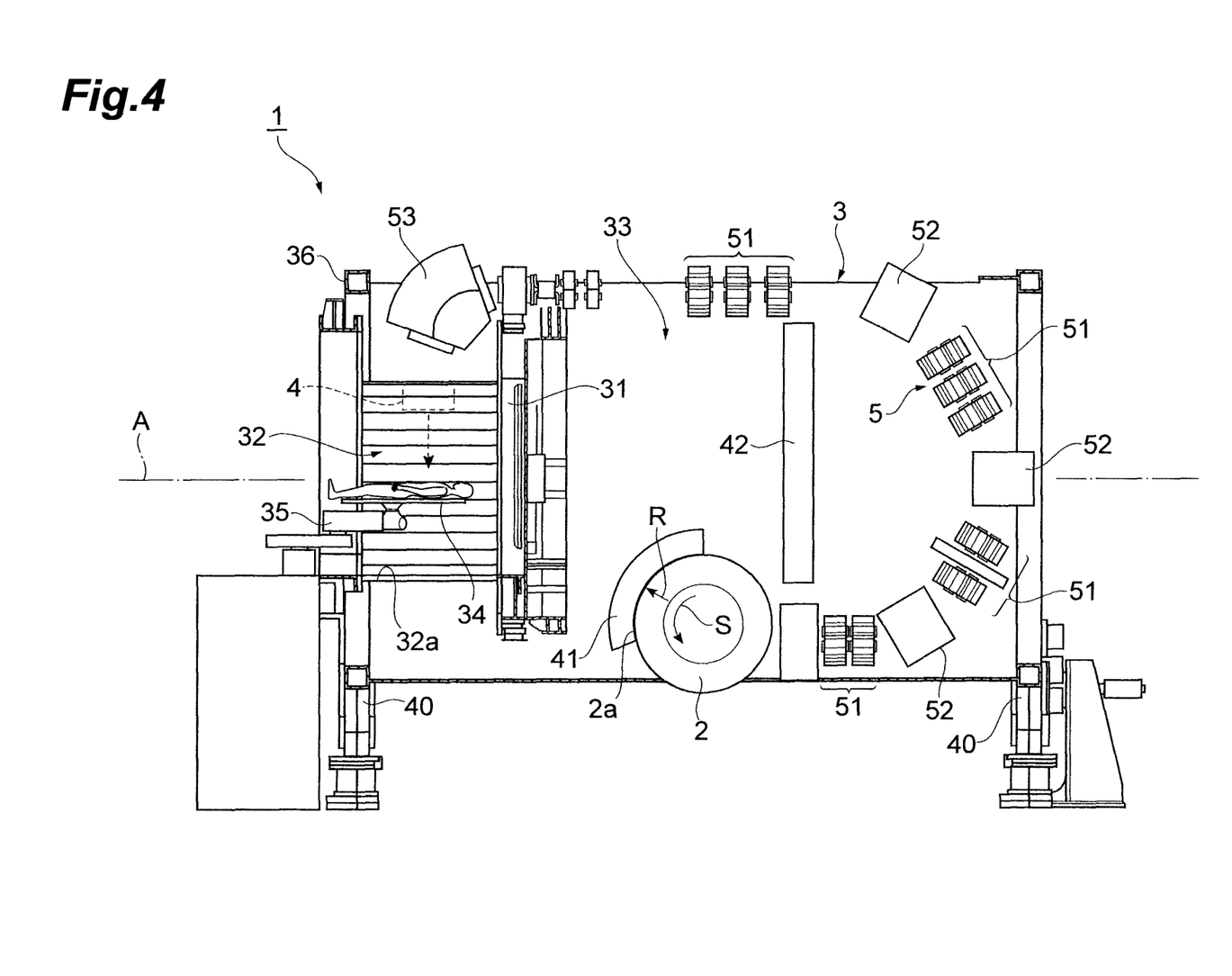
FIG. 4 is a vertical cross-sectional view of a proton therapy system according to another embodiment.

Next, the proton therapy system 1 according to a second embodiment will be described with reference to FIG. 4. FIG. 4 is a vertical cross-sectional view along the axis of rotation of the proton therapy system 1 according to the second embodiment. The proton therapy system 1 according to the second embodiment shown in FIG. 4 is different from the proton therapy system 1 according to the first embodiment shown in FIG. 3 in that a shielding shield 42 is further provided between the ESSs 52 and the treatment table 34.

The shielding shield 42 is for preventing secondary radiation which is generated from the ESSs 52 from advancing in the direction in which the treatment table 34 is present. The shielding shield 42 may also be directly supported on the outer shell section 3 and may also be configured to be supported on the outer shell section 3 through other members. The shielding shield 42 may also be made of the same material as that of the shielding shield 41 provided on the side of the cyclotron 2 and may also be made of a material different from that of the shielding shield 41.

The shielding shield 42 is disposed so as to intersect the axis of rotation A of the gantry, for example. The shielding shield 42 is disposed between the cyclotron 2 and the plurality of ESSs 52 in the axial direction A. In the proton therapy system 1 according to this embodiment, a configuration is made such that the secondary radiation which is generated from the plurality of ESSs 52 is shielded by a single shielding shield 42.

In the proton therapy system 1 according to the second embodiment, because of a configuration in which in addition to the shielding shield 41 disposed so as to cover the side of the cyclotron 2, the shielding shield 42 disposed between the treatment table 34 and the ESSs 52 is provided, it is possible to suppress exposure of a patient to the secondary radiation generated from the ESSs 52. In the ESSs 52, the secondary radiation is generated from the charged particles which collide with the ESSs 52 without passing through the ESSs 52. However, the secondary radiation can be shielded by the shielding shield 42.

Third Embodiment

Figure 5:
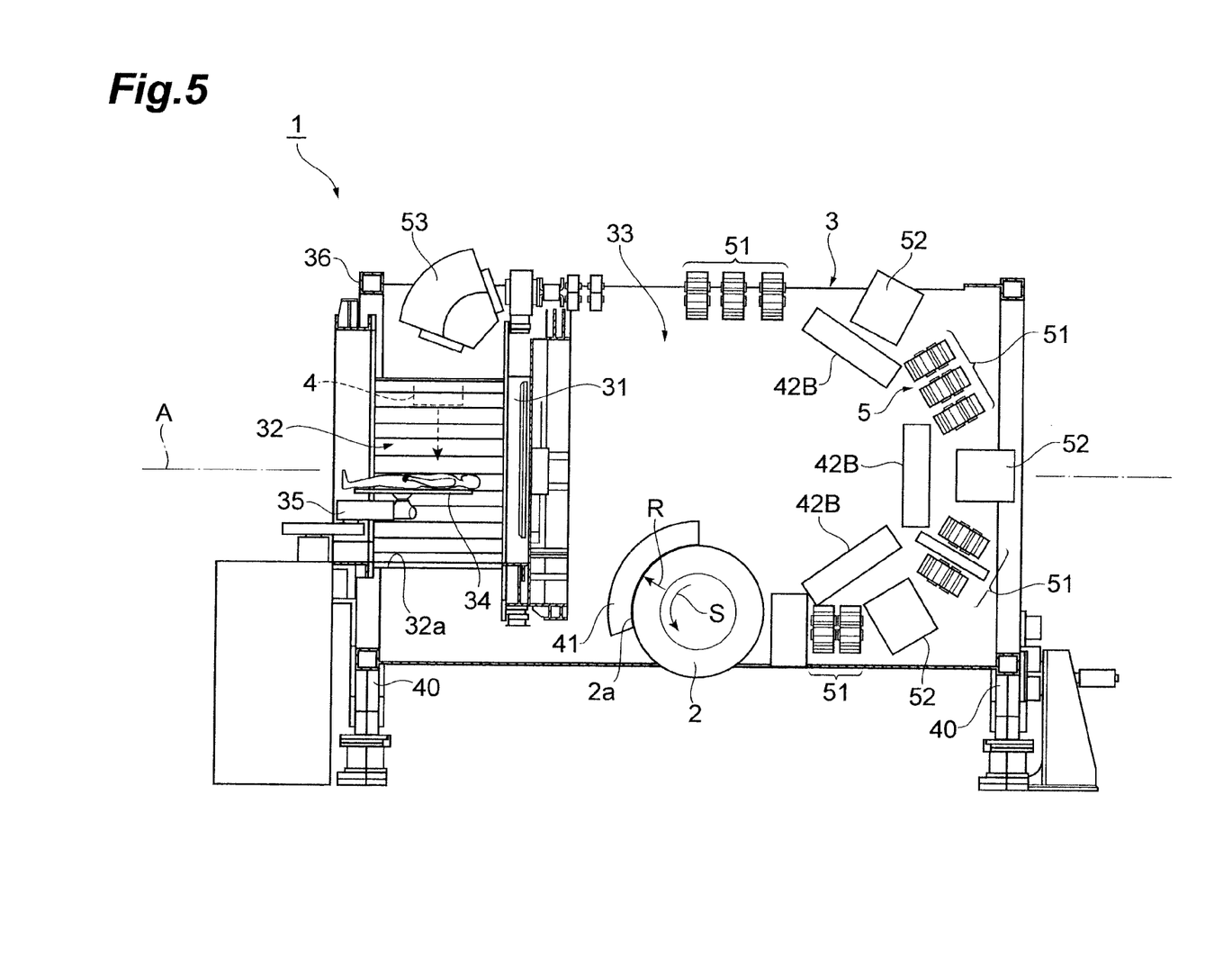
FIG. 5 is a vertical cross-sectional view of a proton therapy system according to still another embodiment.

Next, the proton therapy system 1 according to a third embodiment will be described with reference to FIG. 5. FIG. 5 is a vertical cross-sectional view along the axis of rotation of the proton therapy system 1 according to the third embodiment. The proton therapy system 1 according to the third embodiment shown in FIG. 5 is different from the proton therapy system 1 according to the second embodiment shown in FIG. 4 in that in place of the configuration of shielding the radiation from the plurality of ESSs 52 by the single shielding shield 42, a configuration is made such that the radiation from the plurality of ESSs 52 is shielded by a plurality of shielding shields 42B.

The shielding shield 42B is for preventing the secondary radiation which is generated from the ESSs 52 from advancing in the direction in which the treatment table 34 is present. The shielding shields 42B may also be directly supported on the outer shell section 3 and may also be configured to be supported on the outer shell section 3 through other members. Each shielding shield 42B may also be configured to be fixed to each ESS 52, for example. The shielding shield 42B may also be made of the same material as that of the shielding shield 41 provided on the side of the cyclotron 2 and may also be made of a material different from that of the shielding shield 41.

The plurality of shielding shields 42B is respectively disposed so as to correspond to the ESSs 52. For example, each shielding shield 42B is disposed to face the side surface on the treatment table 34 side of each ESS 52. In the proton therapy system 1 according to this embodiment, a configuration is made such that the plurality of shielding shields 42B respectively shields the secondary radiation which is generated from the ESSs 52 facing thereto.

In the proton therapy system 1 according to the third embodiment, because of a configuration in which in addition to the shielding shield 41 disposed so as to the side of the cyclotron 2, the plurality of shielding shields 42B is disposed between the treatment table 34 and the ESSs 52 is provided, it is possible to suppress exposure of a patient to the secondary radiation generated from the ESSs 52. In the ESSs 52, the secondary radiation is generated from the charged particles which collide with the ESSs 52 without passing through the ESSs 52. However, the secondary radiation can be shielded by the shielding shields 42B.

Further, in the proton therapy system 1 according to this embodiment, since it is possible to dispose each of the shielding shields 42B divided into a plurality to be closer to each of the ESSs 52, it is possible to secure a space for accommodating other devices (for example, a PET camera and the like) in the outer shell section 3.

Fourth Embodiment

Figure 6:
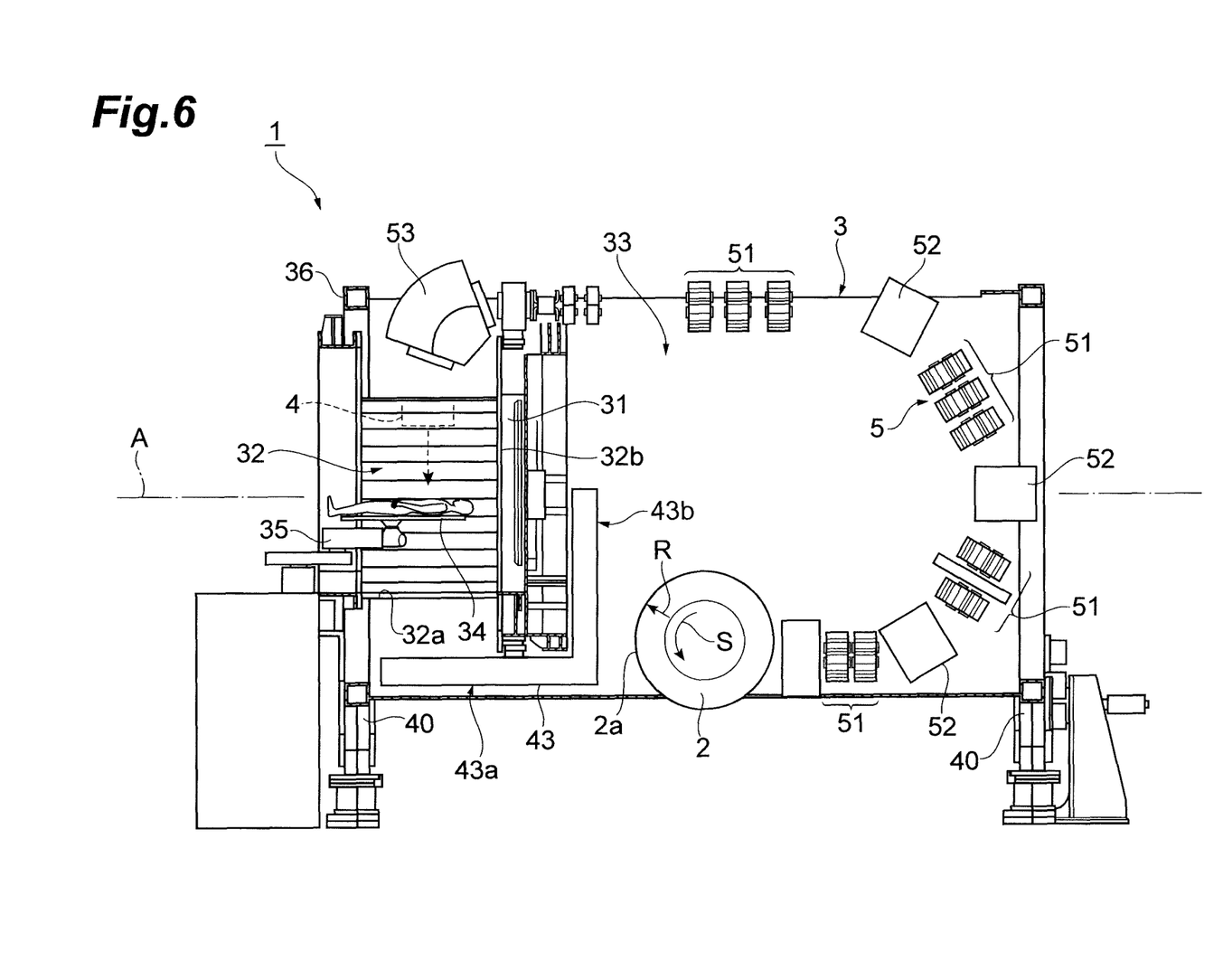
FIG. 6 is a vertical cross-sectional view of a proton therapy system according to still yet another embodiment.

Next, the proton therapy system 1 according to a fourth embodiment will be described with reference to FIG. 6. FIG. 6 is a vertical cross-sectional view along the axis of rotation of the proton therapy system 1 according to the fourth embodiment. The proton therapy system 1 according to the fourth embodiment shown in FIG. 6 is different from the proton therapy system 1 according to the first embodiment shown in FIG. 3 in that in place of the shielding shield 41 disposed so as to cover the side 2a of the cyclotron 2, a shielding shield 43 disposed so as to cover a floor 32a which partitions the area for treatment 32 (an enclosure) and the partition plate (a wall section constituting the irradiation chamber) 31, from the cyclotron 2 side, is provided.

The shielding shield 43 is disposed so as to cover the floor 32a of the enclosure and a partition wall 32b from the cyclotron 2 side. Specifically, the shielding shield 43 includes a shielding plate 43a disposed below the floor 32a and a shielding plate 43b disposed on the backside (the opposite side to the area for treatment 32) of the partition wall 32b. The shielding plate 43a is fixed to the lower surface of the floor 32a and the shielding plate 43b is fixed to the back of the partition wall 32b. The shielding plates 43a and 43b are formed in an integrated fashion, for example. In this manner, the shielding shield may also be configured so as not to be supported on the side 2a of the cyclotron 2. In a case where the shielding shield 43 is not supported on the cyclotron 2, when performing maintenance of the cyclotron 2, since there is no need to remove the shielding shield 43, it is possible to attain improvement in efficiency of work, so that it is possible to easily perform the maintenance.

Since the shielding shield 43 does not rotate along with the gantry (the outer shell section 3), but is fixed to the floor 32a and the partition plate 31, it is possible to reduce a driving force required for rotation of the gantry.

Fifth Embodiment

Figure 7:
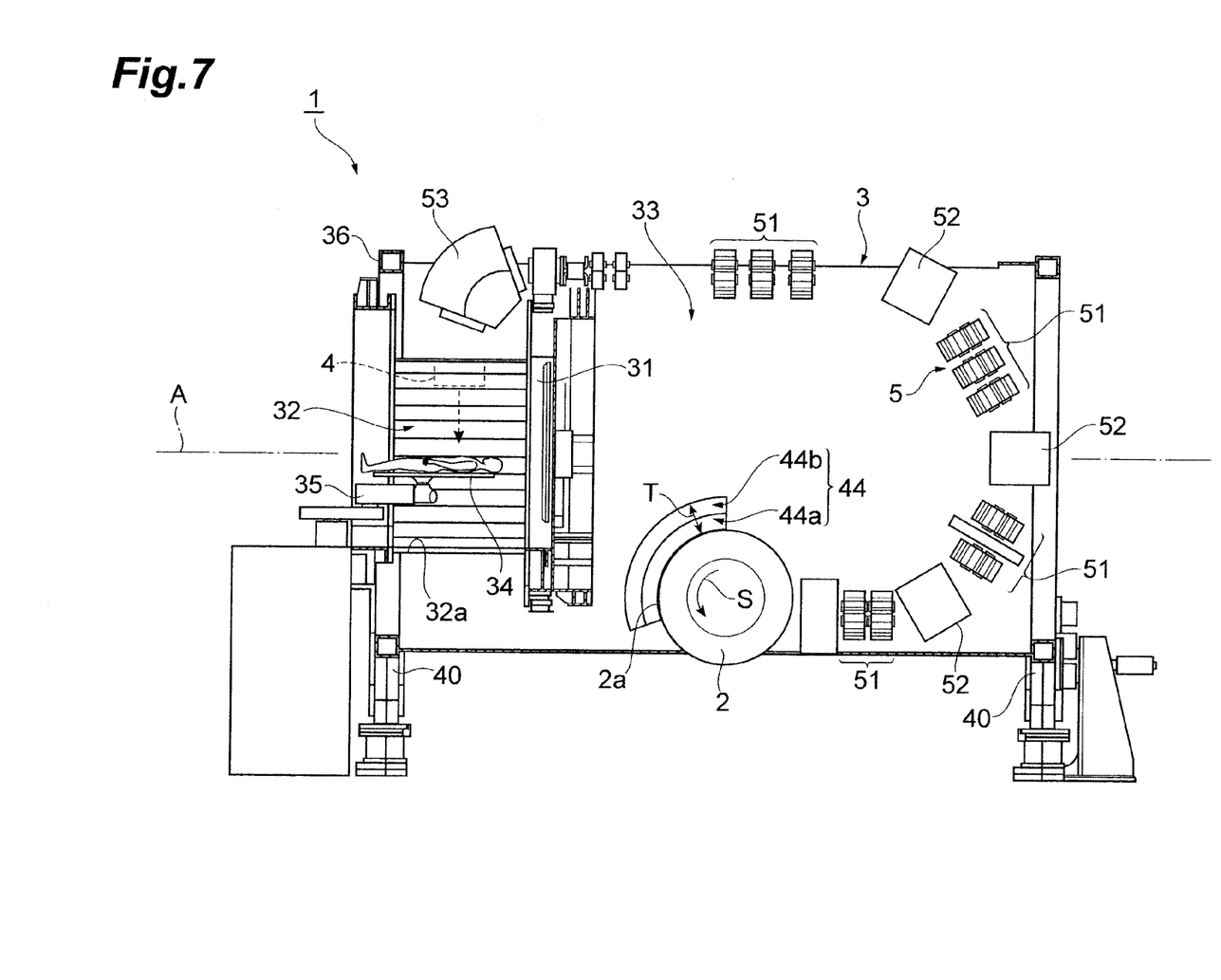
FIG. 7 is a vertical cross-sectional view of a proton therapy system according to further embodiment.

Next, the proton therapy system 1 according to a fifth embodiment will be described with reference to FIG. 7. FIG. 7 is a vertical cross-sectional view along the axis of rotation of the proton therapy system 1 according to the fifth embodiment. The proton therapy system 1 according to the fifth embodiment shown in FIG. 7 is different from the proton therapy system 1 according to the first embodiment shown in FIG. 3 in that a shielding shield 44 configured by laminating a plurality of materials is provided.

The shielding shield 44 is configured by laminating a plurality of different materials in the thickness direction T of the shielding shield 44. As the material which is disposed in each layer of the shielding shield 44, for example, iron, polyethylene, or the like can be given. In the shielding shield 44, for example, iron is disposed as a shielding material 44a on the inner side that is the cyclotron 2 side, and polyethylene is disposed as a shielding material 44b on the outer side. In this manner, by disposing a material in which ability to shield the secondary radiation having high energy is high on the side surface side of the cyclotron 2 and disposing a material in which ability to shield the secondary radiation having low energy is high on the outer side, it is possible to reduce the size of the shielding shield 44. As a result, it is possible to suppress an increase in production costs. Similarly, the shielding shields 42 and 43 shown in FIGS. 4, 5, and 6 may also be configured by a plurality of different materials.

Sixth Embodiment

Figure 8:
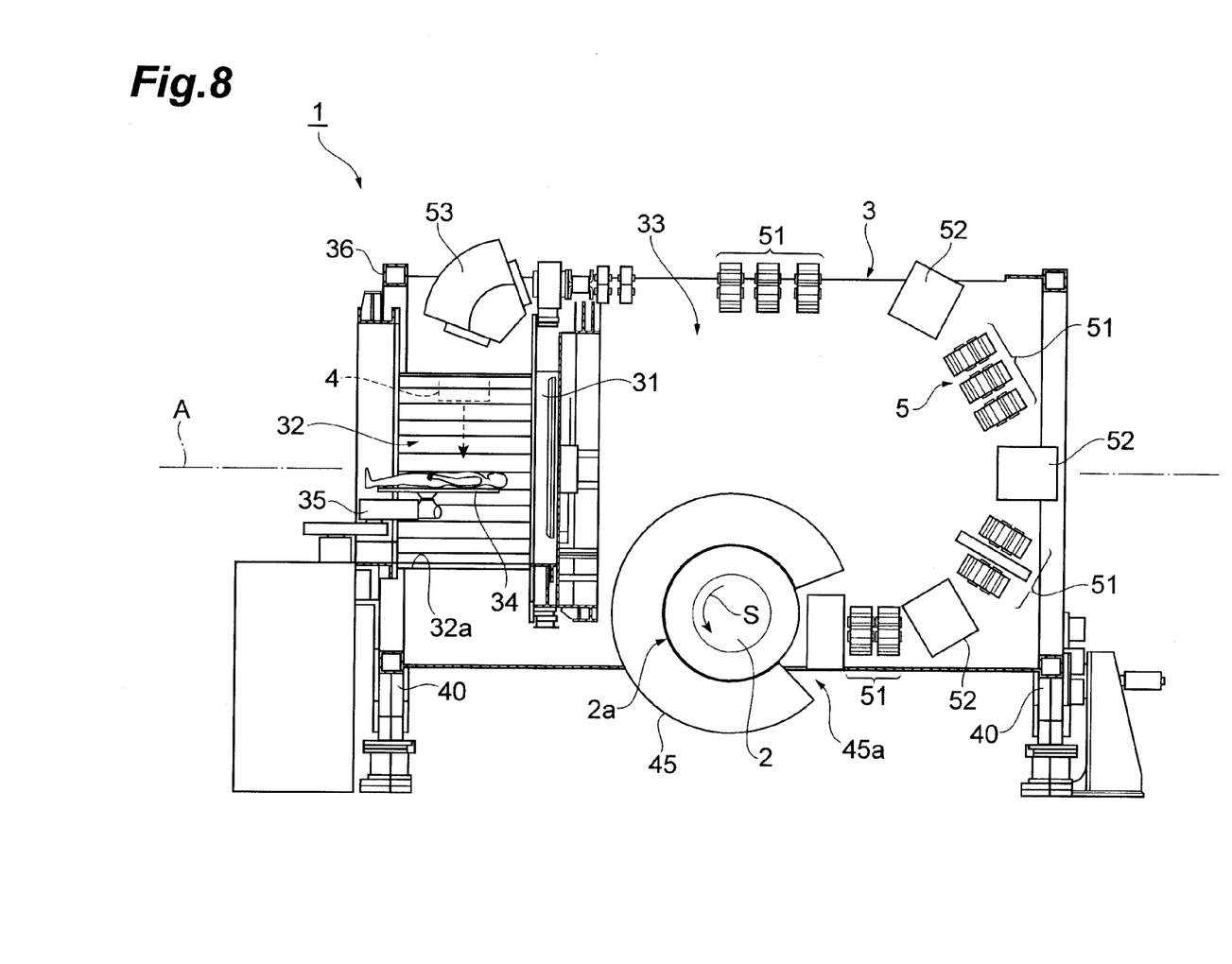
FIG. 8 is a schematic configuration diagram showing a proton therapy system according to still further embodiment.

Next, the proton therapy system 1 according to a sixth embodiment will be described with reference to FIG. 8. FIG. 8 is a vertical cross-sectional view along the axis of rotation of the proton therapy system 1 according to the sixth embodiment. The proton therapy system 1 according to the sixth embodiment shown in FIG. 8 is different from the proton therapy system 1 according to the first embodiment shown in FIG. 3 in that a shielding shield 45 disposed so as to cover the entire circumference of the side 2a of the cyclotron 2 is provided and a cutout portion 45a is formed on the charged particle beam emitting opening side. In this manner, a configuration is also acceptable in which the shielding shield 45 is disposed so as to cover the entire circumference of the side 2a of the cyclotron 2 and a shielding body is not disposed by forming the cutout portion 45a on the charged particle beam emitting opening side. In this way, it is possible to shield the secondary radiation which is radiated in a direction different from the direction in which the treatment table 34 is present. Further, it is also possible to suppress exposure by slight secondary radiation which is reflected in the outer shell section 3.

Seventh Embodiment

Figure 9:
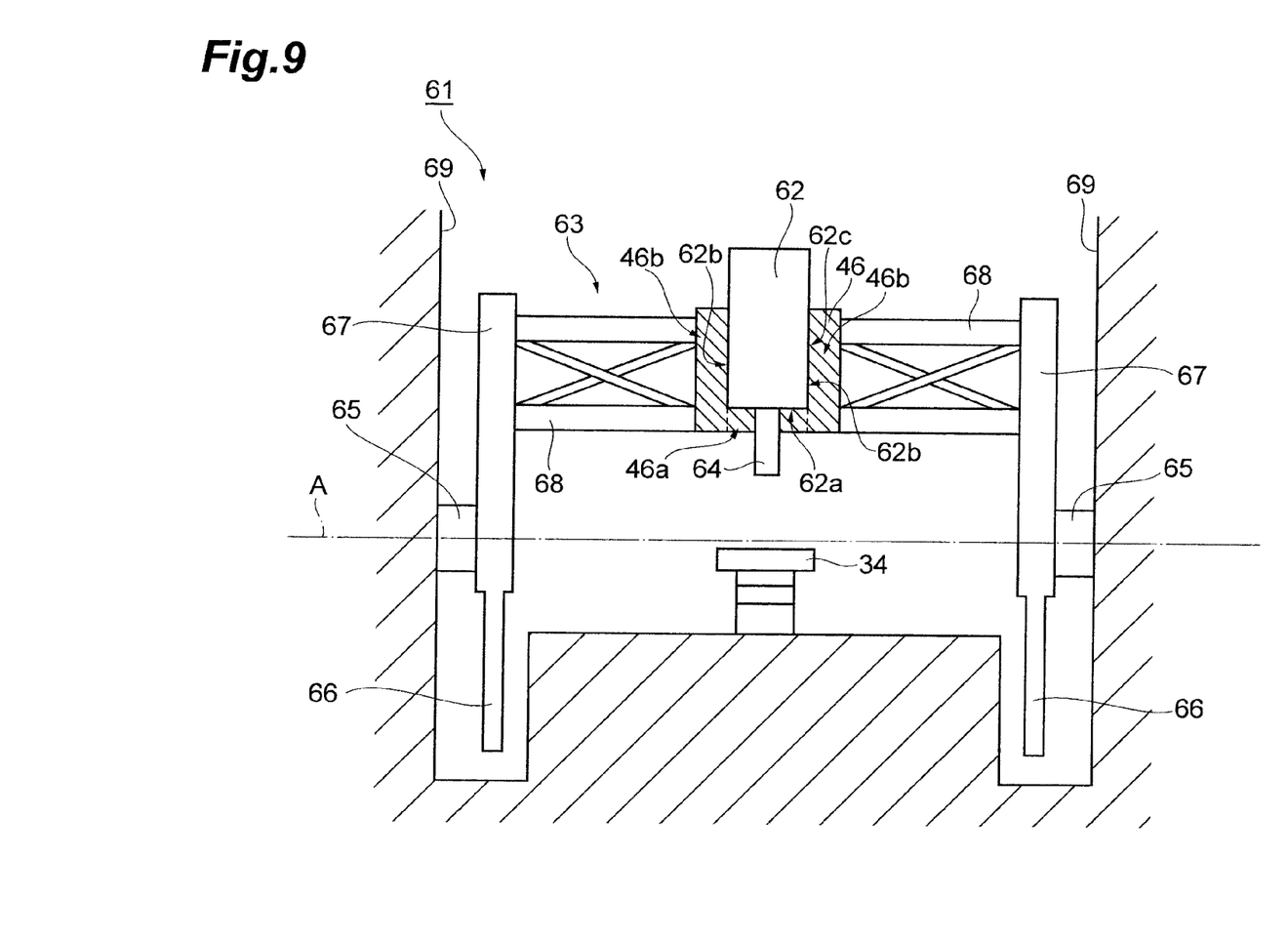
FIG. 9 is a schematic configuration diagram showing a proton therapy system according to still yet further embodiment.
Figure 10:
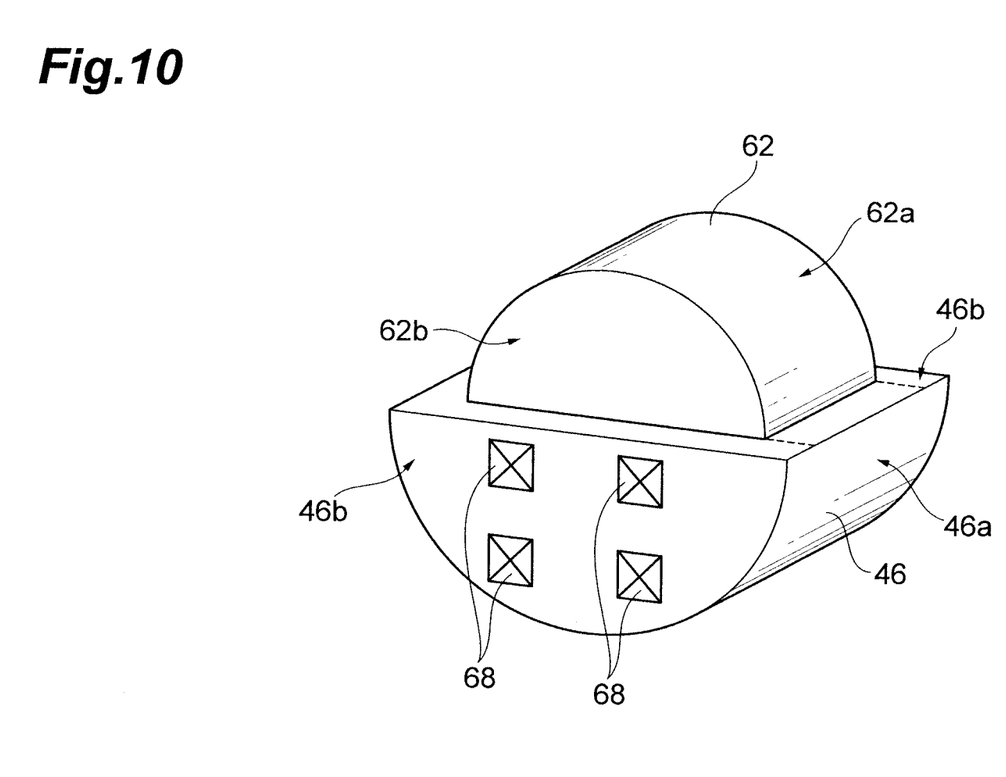
FIG. 10 is a perspective view showing a synchro-cyclotron in FIG. 9 and a shielding shield provided on the side surface of the synchro-cyclotron.

Next, a proton therapy system 61 according to a seventh embodiment will be described with reference to FIG. 9. FIG. 9 is a schematic configuration diagram showing the proton therapy system 61 according to the seventh embodiment, and FIG. 10 is a perspective view showing a synchro-cyclotron 62 in FIG. 9 and a shielding shield 46 provided on a side of the synchro-cyclotron 62. The proton therapy system 61 according to the seventh embodiment shown in FIG. 9 is provided with a gantry 63 of a type different from that in the proton therapy system 1 according to the first embodiment shown in FIG. 3. Further, the proton therapy system 61 is provided with the synchro-cyclotron (a particle accelerator) 62 in place of the cyclotron 2, and the shielding shield 46 which shields the radiation is provided on a side 62a of the synchro-cyclotron 62.

The gantry 63 includes a pair of rotary shafts 65 extending on the same axis (the given axis A) and disposed on both sides with the treatment table 34 interposed therebetween, a pair of leg sections 67 respectively extending upward from the rotary shafts 65, a pair of beam sections 68 extending in a direction of the given axis A between the pair of leg sections 67 and supporting the synchro-cyclotron 62 from both sides, and a pair of counter weights 66 respectively extending downward from the rotary shafts 65.

Wall bodies 69 of a building are disposed to face each other in the direction of the given axis A with the treatment table 34 interposed therebetween. Each of the rotary shafts 65 is supported on each of the wall bodies 69 of the building so as to be able to rotate around the given axis A. Each of the leg sections 67 extends from an end portion on the treatment table 34 side of each of the rotary shafts 65 to the upper side in the illustration. Each of the counter weights 66 extends in the opposite direction to each leg section 67 from an end portion on the treatment table 34 side of each of the rotary shafts 65 to the lower side in the illustration.

The beam sections 68 are respectively supported by the leg sections 67 at positions spaced outwardly from the rotary shafts 65. The beam sections 68 extend in the direction of the given axis A and the synchro-cyclotron 62 is fixed to end portions of the beam sections 68 on the opposite side to the leg sections 67.

As shown in FIGS. 9 and 10, the synchro-cyclotron 62 is provided with a cylindrical casing. A top surface 62b and a bottom surface 62c of the synchro-cyclotron 62 are disposed to face each other in the direction of the given axis A, and the side 62a extends in a circumferential direction surrounding the central axis direction extending in the direction of the given axis A. The shielding shield 46 is provided on the treatment table 34 side (the lower side in the illustration) in the side of the synchro-cyclotron 62, For example, the lower half of the synchro-cyclotron 62 is covered by the shielding shield 46. The shielding shield 46 is disposed so as to cover the lower half of the side 62a of the synchro-cyclotron 62, the lower half of the top surface 62b, and the lower half of the bottom surface 62c. The beam sections 68 may also directly support the synchro-cyclotron 62 and may also indirectly support the synchro-cyclotron 62 through the shielding shield 46. In addition, the shielding shield 46 may also have a configuration in which it is provided with only a shielding body portion 46a covering the lower half of the side 62a and is not provided with shielding body portions 46b covering the lower halves of the top surface 62b and the bottom surface 62c.

In this manner, in the proton therapy system 61 which is provided with the synchro-cyclotron 62, a configuration is also acceptable in which the shielding shield 46 is disposed between the side of the synchro-cyclotron 62 and the treatment table 34. Further, a shielding shield may also be disposed so as to cover the entire surface of the synchro-cyclotron 62.

Eighth Embodiment

Figure 11:
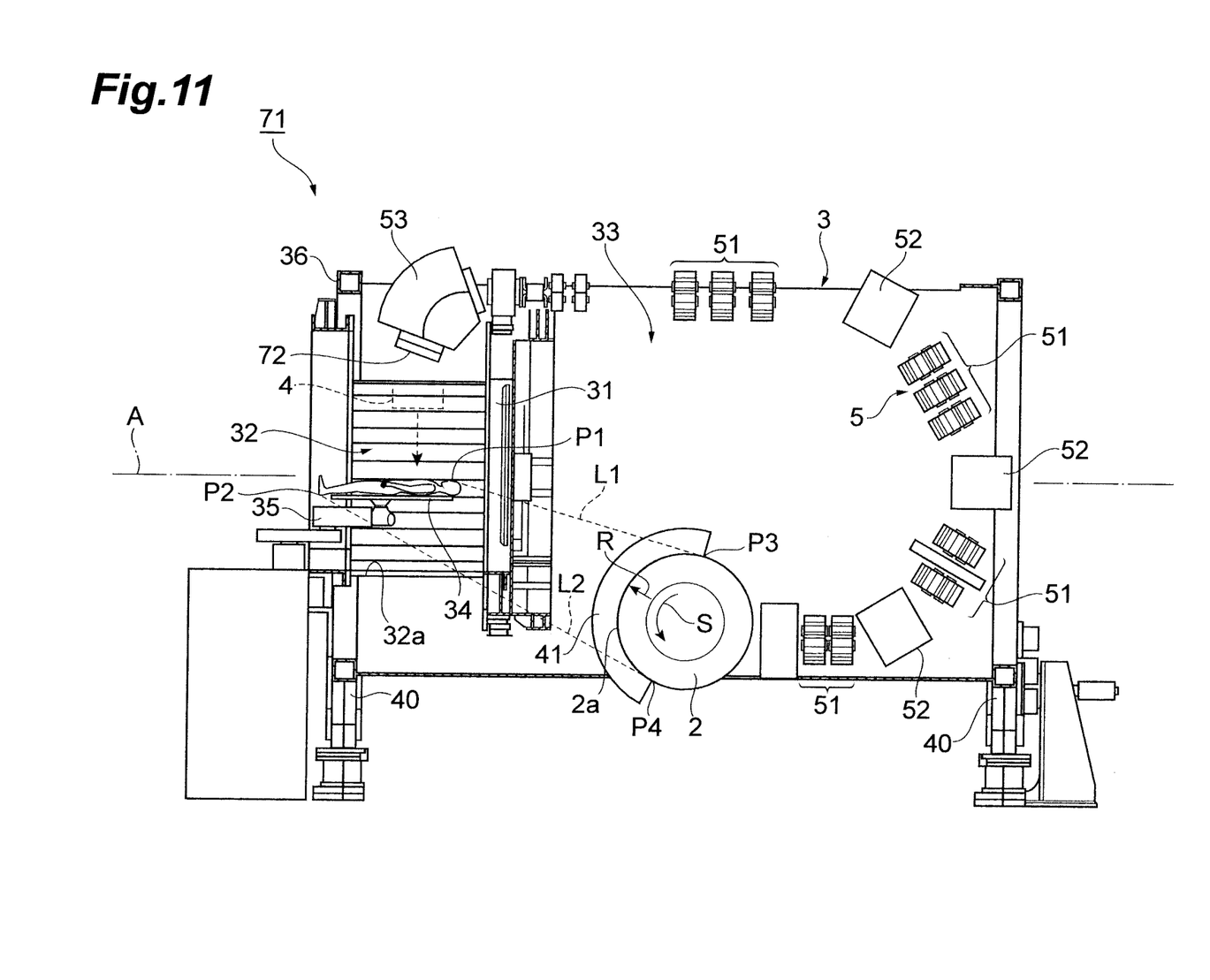
FIG. 11 is a schematic configuration diagram showing a neutron beam therapy system according to still yet further embodiment.

Next, a neutron beam irradiation system 71 according to an eighth embodiment will be described with reference to FIG. 11. FIG. 11 is a schematic configuration diagram showing the neutron beam therapy system according to the eighth embodiment. The neutron beam irradiation system 71 shown in FIG. 11 is different from the proton therapy system 1 shown in FIG. 3 in that a target (a neutron beam generation section) 72 which generates a neutron beam is provided.

The target 72 is provided at a leading end (the outlet side) of the bending magnet 53. The target 72 is irradiated with a proton beam, thereby generating a neutron beam. Then, the irradiation section 4 irradiates the neutron beam generated in the target 72 toward the irradiated body (a patient). The neutron beam is irradiated with respect to a tumor (an irradiation target) in a patient's body, for example.

According to the neutron beam irradiation system 71, similarly to the proton therapy systems according to the above-described embodiments, since the shielding shield 41 which shields the radiation is provided between the side 2a of the cyclotron 2 and the treatment table 34 (a patient or the irradiated body), the secondary radiation which is radiated from the side 2a of the cyclotron 2 is shielded by the shielding body. In this way, since the secondary radiation which is generated due to collision of the charged particles with components such as a magnetic pole or an electrode in the cyclotron 2 is shielded by the shielding shield 41, it is possible to suppress exposure of a patient to the secondary radiation which is radiated from the side 2a. In addition, the shielding shield which is installed in the neutron beam irradiation system 71 is not limited to the shielding shield 41 shown in FIG. 8, and a neutron beam irradiation system which is provided with any of the shielding shields 42 to 46 and 42B as shown in FIGS. 4 to 9 is also acceptable.

Although the exemplary embodiments have been described above in detail, the present invention is not limited to the above-described exemplary embodiments. For example, each element constituting the transport line 5 can be appropriately changed in disposition or the number thereof depending on desired beam design.

Further, the particle accelerator is not limited to the cyclotron and may also be a synchrotron or a synchro-cyclotron. In the case of the synchrotron, the charged particles are accelerated along an orbit revolving on the same circumference, rather than a spiral orbit. Further, the particle radiation (the charged particles) is not limited to a proton beam and may also be a carbon beam (a baryon beam, heavy ion beam) or the like. Further, the shape of the outer shell section 3 is not limited to a circular cylinder and may also be any other tubular shape.

Further, the shielding shield is not limited to a shield covering the side of the accelerator and is acceptable provided that it is disposed between the side of the accelerator and a patient (the treatment table). Further, the shielding shield may also have a configuration in which it is disposed inside a casing which forms an outer shell of the accelerator.

The gantry is not limited to a gantry which rotates (oscillates) 360° and may also be a gantry which performs oscillation by an angle less than 360°.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation system comprising:
    an accelerator which accelerates charged particles along an orbit, thereby emitting a charged particle beam;
    a gantry on which the accelerator is mounted and which can rotate or oscillate around a given axis; and
    an irradiation section which is mounted on the gantry and can irradiate the charged particle beam emitted from the accelerator, toward an irradiated body,
    wherein a radiation shielding body which is provided on the gantry and shields secondary radiation that is radiated from a side of the accelerator, which is a face intersecting a radial direction of the orbit, is disposed, the radiation shielding body is fixedly provided on the gantry.

2. The charged particle beam irradiation system according to claim 1, wherein the shielding body is disposed at a position where only the radiation which is radiated from the portion of the side that faces the irradiated body is shielded, in a circumferential direction of the orbit.

3. The charged particle beam irradiation system according to claim 1, wherein the irradiation system includes an irradiation chamber which is provided in the gantry and in which the irradiated body is irradiated with the charged particle beam, and
    the shielding body is supported on a wall section constituting the irradiation chamber.

4. The charged particle beam irradiation system according to claim 1, wherein the shielding body is disposed so as to cover the entire circumference of the side of the accelerator, and
    a cutout portion is formed on a charged particle beam emitting opening side of the shielding body.

5. The charged particle beam irradiation system according to claim 1, further comprising:
    an energy selection section which is provided on a transport line transporting the charged particles emitted from the accelerator and makes a charged particle having a desired energy width among the charged particles selectively pass therethrough; and
    another shielding body which shields the radiation is disposed between the energy selection section and the irradiated body.

6. The charged particle beam irradiation system according to claim 1, wherein the shielding body is configured by laminating a plurality of different materials in a thickness direction of the shielding body.

7. A neutron beam irradiation system comprising:
    an accelerator which accelerates charged particles along an orbit, thereby emitting a charged particle beam;
    a gantry on which the accelerator is mounted and which can rotate or oscillate around a given axis;
    a neutron beam generation section which is irradiated with the charged particle beam emitted from the accelerator, thereby generating a neutron beam; and
    an irradiation section which is mounted on the gantry and can irradiate the neutron beam generated in the neutron beam generation section, toward an irradiated body,
    wherein a radiation shielding body which is provided on the gantry and shields secondary radiation that is radiated from a side of the accelerator, which is a face intersecting a radial direction of the orbit, is disposed, the radiation shielding body is fixedly provided on the gantry.

* * * * *